(12) United States Patent
Hayzelden et al.

(10) Patent No.: US 6,605,086 B2
(45) Date of Patent: Aug. 12, 2003

(54) STEERABLE CATHETER WITH TORQUE TRANSFER SYSTEM

(75) Inventors: Robert C. Hayzelden, Canyon Lake, CA (US); John A. Simpson, Carlsbad, CA (US); Wade A. Bowe, Temecula, CA (US); Andrea M. Moore, Murrieta, CA (US); Jesse Flores, Perris, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 40 days.

(21) Appl. No.: 09/848,114

(22) Filed: May 2, 2001

(65) Prior Publication Data

US 2002/0165534 A1 Nov. 7, 2002

(51) Int. Cl.$^7$ ............................................. A61B 18/18
(52) U.S. Cl. ..................... 606/41; 604/95.04; 604/95.05
(58) Field of Search ........................... 606/41; 600/374, 600/585; 607/122; 604/95.04, 95.05

(56) References Cited

U.S. PATENT DOCUMENTS

| | | |
|---|---|---|
| 3,521,620 A | 7/1970 | Cook |
| 4,886,067 A | 12/1989 | Palermo |
| 4,921,482 A | 5/1990 | Hammerslag et al. |
| 4,979,510 A | 12/1990 | Franz et al. |
| 4,998,916 A | 3/1991 | Hammerslag et al. |
| 5,037,391 A | 8/1991 | Hammerslag et al. |
| 5,108,368 A | 4/1992 | Hammerslag et al. |
| 5,125,896 A | 6/1992 | Hojeibane |
| 5,195,968 A | 3/1993 | Lundquist et al. |
| 5,228,441 A | 7/1993 | Lundquist |
| 5,254,088 A | 10/1993 | Lundquist et al. |
| 5,273,535 A | 12/1993 | Edwards et al. |
| 5,315,996 A | 5/1994 | Lundquist |
| 5,318,525 A | 6/1994 | West et al. |
| 5,318,526 A | 6/1994 | Cohen |
| 5,322,064 A | 6/1994 | Lundquist |
| 5,327,905 A | 7/1994 | Avitall |
| 5,329,923 A | 7/1994 | Lundquist |
| 5,334,145 A | 8/1994 | Lundquist et al. |
| 5,336,182 A | 8/1994 | Lundquist et al. |
| 5,358,478 A | 10/1994 | Thompson et al. |
| 5,358,479 A | 10/1994 | Wilson |
| 5,363,861 A | 11/1994 | Edwards et al. |
| 5,368,564 A | 11/1994 | Savage |
| 5,372,587 A | 12/1994 | Hammerslag et al. |
| 5,383,852 A | 1/1995 | Stevens-Wright |

(List continued on next page.)

OTHER PUBLICATIONS

Grafton A. Smith, M.D., and Edward L. Brackney, M.D., "Preliminary Report on a New Method of Intestinal Intubation with the Aid of a Flexible Stylet with Controllable Tip," Dept. of Surgery, University of Minnesota Medical School, Surgery, vol. 27, #6, Jun. 1950.

*Primary Examiner*—Michael Peffley
(74) *Attorney, Agent, or Firm*—Fulwider Patton Lee & Utecht, LLP

(57) ABSTRACT

A catheter includes a steering mechanism for manipulating the distal end of the catheter to obtain a plurality of deflection profiles, and a torque transfer system at the distal portion to enhance torque transfer from the handle to the distal tip. The steering mechanism includes two steering tendons. The steering tendons are attached to the distal-end region of the catheter. The steering tendons may be located approximately angularly aligned, thus causing the deflection profiles to be unidirectional. Alternatively, the steering tendons may be located angularly separated from each other, thus causing the deflection profiles to be bidirectional. In other aspects, the torque transfer system includes a flat ribbon within the relatively flexible distal-end region to enhance torque transfer through the distal-end region of the catheter.

32 Claims, 6 Drawing Sheets

U.S. PATENT DOCUMENTS

| | | |
|---|---|---|
| 5,383,923 A | 1/1995 | Webster, Jr. |
| 5,395,327 A | 3/1995 | Lundquist et al. |
| 5,478,330 A | 12/1995 | Imran et al. |
| 5,487,757 A | 1/1996 | Truckai et al. |
| 5,489,270 A | 2/1996 | van Erp |
| 5,496,260 A | 3/1996 | Krauter et al. |
| 5,507,725 A | 4/1996 | Savage et al. |
| 5,531,686 A | 7/1996 | Lundquist et al. |
| 5,545,200 A | 8/1996 | West et al. |
| 5,603,697 A | 2/1997 | Grundy et al. |
| 5,642,736 A | 7/1997 | Avitall |
| 5,643,255 A | 7/1997 | Organ |
| 5,674,197 A | 10/1997 | van Muiden et al. |
| 5,687,723 A | 11/1997 | Avitall |
| 5,755,760 A | 5/1998 | Maguire et al. |
| 5,782,828 A | 7/1998 | Chen et al. |
| 5,797,842 A | 8/1998 | Pumares et al. |
| 5,810,802 A | 9/1998 | Panescu et al. |
| 5,820,591 A | 10/1998 | Thompson et al. |
| 5,855,552 A | 1/1999 | Houser et al. |
| 5,855,560 A | 1/1999 | Idaomi et al. |
| 5,865,800 A | 2/1999 | Mirarchi et al. |
| 5,882,333 A | 3/1999 | Schaer et al. |
| 5,891,088 A | 4/1999 | Thompson et al. |
| 5,893,885 A | 4/1999 | Webster, Jr. |
| 5,916,147 A | 6/1999 | Boury |
| 5,928,191 A | 7/1999 | Houser et al. |
| 5,944,689 A | 8/1999 | Houser et al. |
| 5,984,907 A | 11/1999 | McGee et al. |
| 6,022,343 A | 2/2000 | Johnson et al. |
| 6,033,378 A | 3/2000 | Lundquist et al. |
| 6,063,077 A | 5/2000 | Schaer |
| 6,142,994 A | 11/2000 | Swanson et al. |
| 6,163,716 A | 12/2000 | Edwards et al. |
| 6,208,881 B1 | 3/2001 | Champeau |

STEERABLE CATHETER WITH TORQUE TRANSFER SYSTEM

BACKGROUND OF THE INVENTION

The invention relates generally to catheters, and more particularly to a catheter having a steerable distal-end region with enhanced distal torque transfer.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery or vein to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate electrophysiological ("EP") catheter system.

One such EP catheter system, as disclosed in U.S. Pat. Nos. 6,059,778 and 6,096,036, includes a plurality of spaced apart band electrodes located at the distal end of the catheter and arranged in a linear array. The band electrodes are positioned proximal heart tissue. RF energy is applied through the electrodes to the heart tissue to produce a series of long linear lesions similar to those produced by the Maze procedure. The catheters currently used for this procedure are typically flexible at the distal end, and the profile at the distal end is adjustable. However, when using such catheters, it is often difficult to conform the distal-end profile to some of the irregular topographies of the interior cavities of the heart. In other instances, it is difficult for a multi-electrode catheter that is designed to produce long linear lesions to access and ablate tissue in regions that require short linear lesions, such as the so-called isthmus region that runs from the tricuspid annulus to the eustachian ridge. Ablation of tissue in this region, and other regions non-conducive to the placement of multi-electrode, long, linear-lesion ablation catheters within them, is best accomplished by delivering RF energy to a tip electrode to produce localized spot lesions or if longer lesions are required, by energizing the tip while it is moved across the tissue.

Other catheters for producing spot lesions or tip-drag lesions typically include a tip ablation electrode and a plurality of mapping band electrodes positioned at the distal end of the catheter. The catheters are steerable in that they are configured to allow the profile of the distal end of the catheter to be manipulated from a location outside the patient's body. Steerable catheters that produce multiple deflection profiles of their distal ends provide a broader range of steerability. However, known steerable catheters, such as that disclosed in U.S. Pat. No. 5,195,968, have steering tendons attached to a ribbon at or near the longitudinal centerline of the catheter. Because of the relatively short distance between the tendon attachment point and the ribbon that resides along the centerline of the catheter sheath, a force applied to the tendon results in a relatively small bending moment for deflecting the distal tip. The ribbon/tendon assembly is typically provided clearance to allow the tendon to become substantially displaced from the centerline as deflection progresses, thereby enlarging the moment arm and consequently increasing the applied bending moment. Unfortunately, this requires such designs to include additional lumen space, translating into larger catheter diameters. Larger diameter catheters are undesirable due to the increased trauma they inflict on a patient. Further, as the tendon displaces to the extent that it contacts the catheter wall, the associated friction may necessitate greater exertion to further deflect the distal tip. Lessening the amount of force required to deflect the distal tip of a catheter by actions outside the catheter is desired in that the catheter tip can more easily be placed in the correct location within a patient.

In addition to deflecting the distal tip, placing the distal portion of a catheter in the correct location within a patient often requires rotation of the catheter from a location outside the body, typically by rotating the handle. However, the sheaths in known steerable catheters have proximal regions with higher torsional strength than their distal-end regions. The reduction in torsional strength from the proximal region to the distal-end region makes accurate rotation of the distal portion difficult and if not carefully controlled, can result in a whip effect of the distal tip. Uncontrolled movement of the distal tip can cause trauma to the patient.

Hence, those skilled in the art have identified a need for a tip-electrode, ablation catheter with a steerable distal-end region that is capable of accessing those areas of the heart which are typically inaccessible by multi-electrode ablation catheters. Needs have also been identified for smaller diameter catheters to improve patient comfort, and for more easily deflected catheters so that they may be more easily used. Additionally, the need for a catheter having sufficient torsional stiffness at its distal end to permit more accurate transfer of rotational movement from the handle to the distal tip has also been identified. The present invention fulfills these needs and others.

SUMMARY OF THE INVENTION

Briefly, and in general terms, the present invention is directed to a catheter with a steerable distal-end region and enhanced distal torque transfer.

In a first aspect, the invention relates to a catheter that includes a sheath having a proximal region, a distal-end region, and a longitudinal centerline. The catheter also includes a first steering tendon housed within the sheath. The first steering tendon has a first end that is attached to the distal-end region at a location offset from the centerline of the sheath, and a second end that is located at the proximal region of the sheath. Movement of the first steering tendon in the proximal direction causes the sheath distal-end region to deflect. The catheter further includes a second steering tendon housed within the sheath. The second steering tendon has a first end that is attached to the distal-end region at a location offset from the centerline of the sheath, and a second end that is located at the proximal region of the sheath. Movement of the second steering tendon in the proximal direction causes the sheath distal-end region to deflect. Additionally, the catheter also includes a torque transfer system that is adapted to transfer torsional forces from the proximal region of the sheath to the distal-end region of the sheath.

In a detailed aspect of the invention, the torque transfer system includes a ribbon that is housed within the distal-end region of the sheath. The ribbon is configured to deflect with the distal-end region of the sheath and has a first end attached to the distal-end region of the sheath and a second end attached to the proximal region of the sheath. In a more detailed aspect, the ribbon is positioned along the centerline of the distal-end region of the sheath. In a further detailed aspect, the ribbon is formed of a resiliently deformable, shape-memory material. In another detailed aspect, the ribbon has a substantially rectangular cross-section and the first steering tendon and the second steering tendon are attached proximate the inner surface of the sheath on opposite sides of the ribbon. In another facet of the invention, the attachment point of the first steering tendon is distal the attachment point of the second steering tendon. In an additional detailed facet, the attachment point of the first steering tendon and the attachment point of the second steering tendon are axially aligned. In a further facet of the invention, the ribbon has a substantially rectangular cross-section and the first steering tendon and the second steering tendon are attached proximate the inner surface of the sheath on the same side of the ribbon. In another aspect of the invention, the torque transfer system further includes an eyelet secured within the proximal region of the sheath and the second end of the ribbon is secured within the eyelet. In a more detailed aspect, the eyelet includes a non-circular shape proximal end having a maximum cross-sectional diameter greater than the inner diameter of the sheath. In a further aspect, the non-circular shape includes a substantially angular shape. In a more detailed aspect, the angular shape includes a substantially hexagonal shape.

In a second aspect, the invention relates to a catheter that includes a sheath having a proximal region and a distal-end region. The catheter also includes a first steering tendon that is housed within the sheath. The first steering tendon has a first end that is attached to the distal-end region at a point proximate the inner surface of the sheath, and a second end that exits the proximal end of the sheath. Movement of the first steering tendon in a proximal direction causes the sheath distal-end region to deflect. The catheter further includes a second steering tendon that is housed within the sheath. The second steering tendon has a first end that is attached to the distal-end region at a point proximate the inner surface of the sheath and proximal the attachment point of the first steering tendon, and a second end that exits the proximal end of the sheath. Movement of the second steering tendon in the proximal direction causes the sheath distal-end region to deflect. Additionally, the catheter also includes a ribbon that is housed within the distal-end region of the sheath and is configured to deflect therewith. The ribbon has a first end that is attached to the distal-end region of the sheath and a second end that is attached to the proximal region of the sheath.

In a detailed aspect of the invention, the ribbon has a substantially rectangular cross-section and the first and second steering tendons are attached on opposite sides of the ribbon. In another aspect, the ribbon has a substantially rectangular cross-section and the first steering tendon and the second steering tendon are attached on the same side of the ribbon. In a more detailed aspect, the first end of the ribbon is secured within the distal tip of the distal-end region. In another facet of the invention, the catheter further includes an eyelet that is housed within the proximal region of the sheath at the distal end of the proximal region wherein the second end of the ribbon is secured within the eyelet. In a further facet, the first steering tendon is secured within the distal tip of the distal-end region. In an additional facet, the catheter further includes an anchor band that is positioned within the distal-end region, proximal the distal tip, wherein the first end of the second steering tendon is attached to the anchor band.

In a third aspect, the invention relates to a catheter for use with biological tissue. The catheter includes a sheath having a proximal region with a first torque transfer strength and a distal-end region with a second torque transfer strength that is less than the first torque transfer strength. The catheter further includes at least one electrode that is located in the distal-end region for transferring energy to the biological tissue. The catheter additionally includes a first steering tendon that is housed within the sheath. The first steering tendon has a first end that is attached to the distal-end region at a point proximate the inner surface of the sheath and a second end that exits the proximal end of the sheath. Movement of the first steering tendon in a proximal direction causes the sheath distal-end region to deflect. The catheter also includes a second steering tendon that is housed within the sheath. The second steering tendon has a first end that is attached to the distal-end region at a point proximate the inner surface of the sheath and proximal to the attachment point of the first steering tendon and a second end that exits the proximal end of the sheath. Movement of the second steering tendon in the proximal direction causes the sheath distal-end region to deflect. The catheter further includes a torque transfer system that is adapted to increase the torque transfer strength of the distal-end region to facilitate the transfer of torsional forces from the proximal region to the distal-end region.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
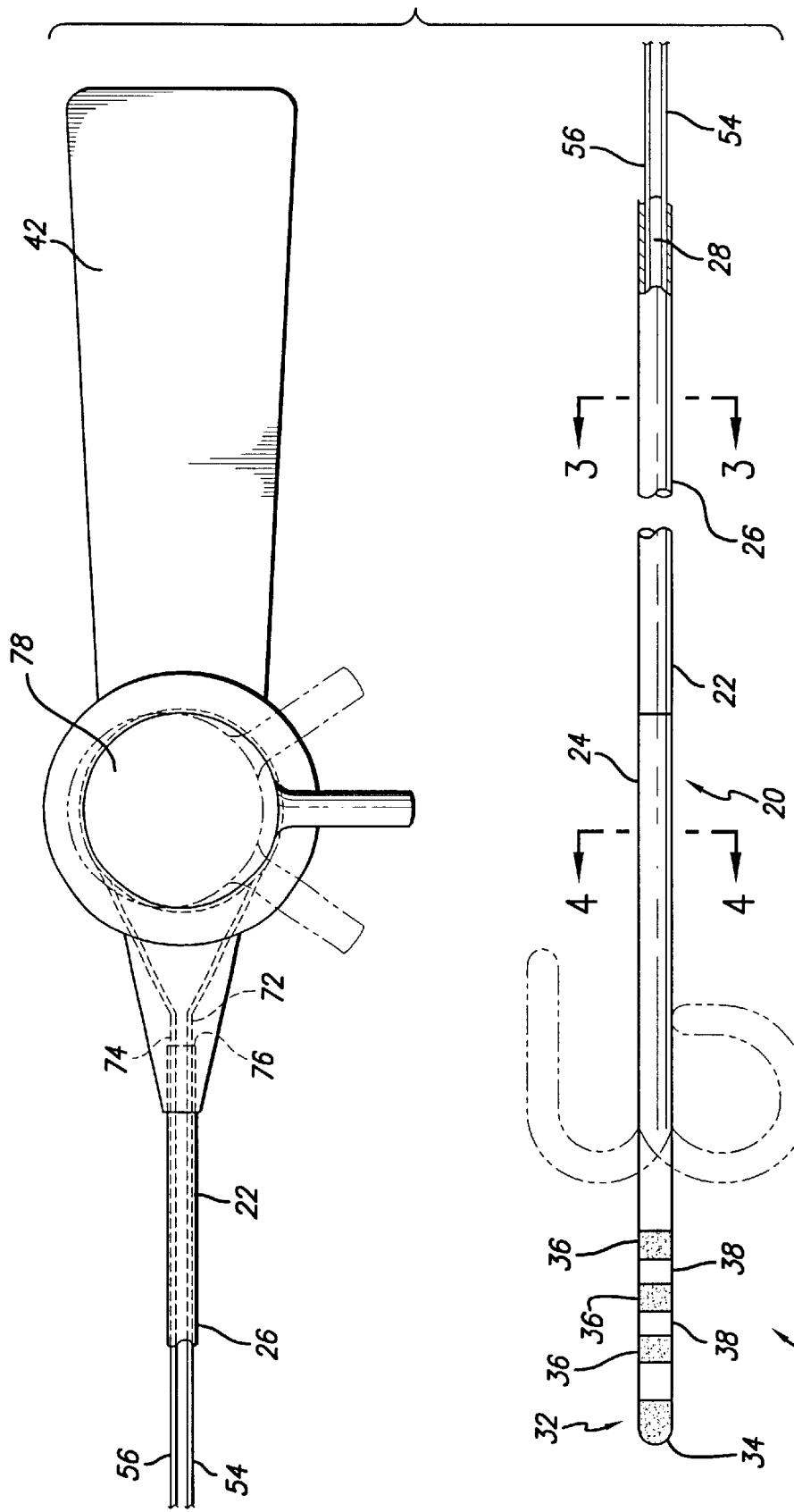
FIG. 1 is a plan view with a broken-out section of a catheter configured in accordance with aspects of the invention and depicting components of the catheter including a sheath, a steering mechanism and a steering handle.

Referring now to the drawings, in which like reference numerals are used to designate like or corresponding elements among the several figures, in FIG. 1 there is shown a catheter 20 incorporating aspects of the present invention. The catheter 20 includes a sheath 22 having a flexible distal-end region 24, a proximal region 26 and an open lumen 28 running throughout. At the distal end 30 of the distal-end region 24 is a distal tip 32. The distal-end region 24 includes a tip electrode 34 for applying ablation energy to a biological site. Located proximal from the tip electrode 34 are three band electrodes 36 arranged in a substantially linear array along the distal-end region 24 of the sheath 22. The band electrodes 36 are arranged so that there is space 38 between adjacent electrodes. In one configuration, the band electrodes 36 are two mm wide and the space 38 between the electrodes is also two mm wide. Alternatively, the band electrodes 36 may be three mm wide and the space 38 between the electrodes may be four mm wide, or other dimensions suitable for mapping and/or ablation procedures. The band electrodes 36 may be used to map the interior surfaces of the heart or to apply ablation energy, or both. The tip electrode 34 may be used to deliver RF energy to the biological site to form spot or tip-drag lesions, or for mapping, or for both.

Figure 2:
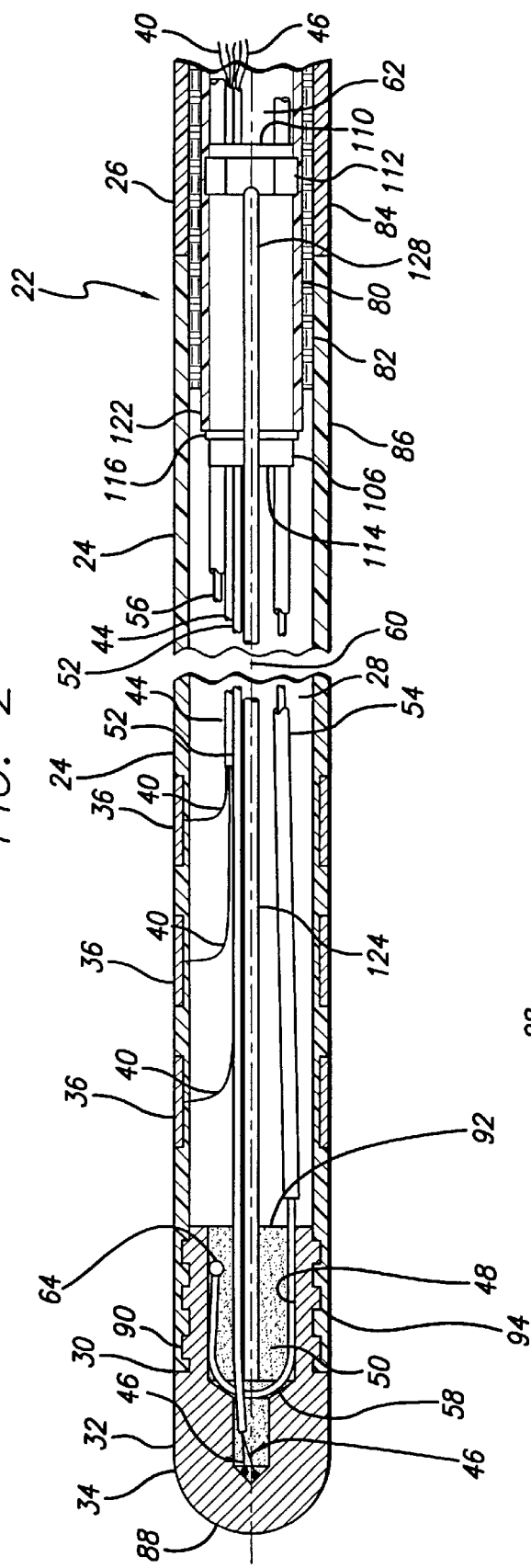
FIG. 2 is a cross-sectional plan view with a broken-out section of the distal portion of the catheter of FIG. 1 depicting detailed components including steering tendons arranged to provide bidirectional steering profile capabilities and a torque transfer system.

Individual lead wires 40 (not shown in FIG. 1) run from the handle 42 to each band electrode 36. With reference to FIG. 2, the lead wires 40 are attached to the band electrodes 36 in a way that establishes good electrical contact, such as by welding. The lead wires 40 are grouped together and enclosed within a sheath 44 that spans the distal-end region 24 proximal the most proximal band electrode 36 and continues into the proximal region 26 of the sheath 22. The sheath 44 is formed of a flexible material, such as a thin-walled heat-shrink tubing, so that it may deflect when needed.

With further reference to FIG. 2, a pair of thermocouple wires 46 run from the handle 42 shown in FIG. 1 through the sheath 22 to a bore 48 within the tip electrode 34. Each of the thermocouple wires 46 is individually attached at the distal end of the bore 48 in the tip electrode 34 in a way that achieves good electrical contact, such as by soldering. By attaching the thermocouple wires 46 to the tip electrode 34 in this manner, the thermocouple effect is achieved through the tip electrode, and good thermal contact is achieved for a more accurate determination of the temperature of the tip electrode. After being attached to the bore 48, the thermocouple wires 46 are potted into the bore with a resin 50, such as epoxy. One of the thermocouple wires 46 also serves as a drive wire to transmit ablation energy to the tip electrode 34. Exemplary configurations of electrodes having combination thermocouple/drive wires are disclosed in U.S. Pat. Nos. 6,049,737 and 6,045,550. The thermocouple wires 46 are grouped together and enclosed within a sheath 52 that spans throughout the distal-end region 24 and continues into the proximal region 26 of the sheath 22. The sheath 52 is formed of a flexible material, such as a thin-walled heat-shrink tubing, so that it may deflect when needed. In an alternate embodiment, the thermocouple wires 46 are twisted and soldered together prior to being soldered into the tip electrode 34. While the thermocouple effect in this configuration does not depend on the tip electrode 34, the attachment of the thermocouple to the tip electrode does provide the wire pair 46 with good thermal contact.

With continued reference to FIG. 2, housed within the sheath 22 is a first steering tendon 54, a second steering tendon 56 and a torque transfer system comprising an eyelet 106 and a flat ribbon 124. The distal end 58 of the first steering tendon 54 is offset from a longitudinal centerline 60 of the sheath 22. In order to apply deflection force directly to the distal tip, the distal end 58 of the first steering tendon 54 is inserted into the bore 48 of the distal tip 32. The distal end 58 is then bonded into place with the resin 50. As will be discussed below in more detail, by placing the distal end 58 of the first steering tendon 54 at a location offset from the longitudinal centerline 60 and therefore proximate the inner surface 62 of the sheath 22, a relatively low amount of force applied to the first steering tendon 54 will generate a bending moment sufficient to deflect the distal-end region 24. To ensure a good bond between the resin 50 and the first steering tendon 54 and good anchoring of the tendon within the tip electrode, the distal end 58 of the first steering tendon is hook-shaped with a ball 64 disposed at the end. As will be discussed below in more detail, in one embodiment the distal end 66 (see FIG. 5) of the second steering tendon 56 is attached to the interior surface wall 68 of an anchor band 70 positioned within the distal-end region 24, which places the second steering tendon proximate the inner surface 62 of the sheath 22. With reference to FIG. 1, the proximal end 72 of the first steering tendon 54 and the proximal end 74 of the second steering tendon 56 exit through the proximal end 76 of the sheath 22, and attach to a steering controller 78 within the handle 42.

Figure 3:
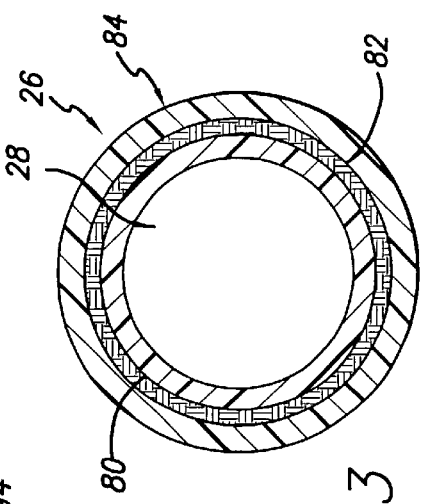
FIG. 3 is a cross-section view of the construction of the proximal region of the sheath taken along the line 3—3 from FIG. 1.

With reference to FIG. 3, which is a cross-sectional view taken from FIG. 1, the proximal region 26 of the sheath 22 is a layered composite. The inner layer 80 is a hollow tube made of a polymer possessing a high modulus of elasticity, such as polyetheretherketone (PEEK). A middle layer 82 having one or more layers of braided, 0.025 mm×0.075 mm stainless steel ribbons is applied upon the inner layer 80 to increase the torque transfer strength of the proximal region 26. Only one layer is shown in FIG. 3 for clarity of illustration. The proximal region's 26 outer layer 84 is made of a flexible, intermediate-durometer polymer such as polyether block amide, known commercially as Pebax™. In one embodiment, the outer layer 84 includes a 63D (shore "D" hardness value) hardness scale Pebax™ tube. The three layers 80, 82, and 84 are bonded together by the simultaneous application of heat and pressure, thus creating a flexible tube with the braided stainless steel ribbons of the middle layer 82 providing superior torsional rigidity. The distal ends of the three layers 80, 82 and 84 are stepped, thus exposing the outer surface of the inner layer and the braided stainless steel ribbons of the middle layer.

Figure 4:
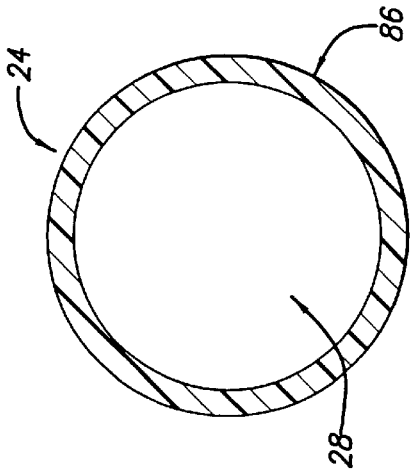
FIG. 4 is a cross-section view of the construction of the distal-end region of the sheath taken along the line 4—4 from FIG. 1.

With reference to FIG. 4, which is a cross-sectional view taken from FIG. 1, the construction of the distal-end region 24 includes a single layer 86 of a lower durometer Pebax™. In one embodiment, the layer 86 includes a 35D hardness scale Pebax™ tube. Accordingly, the distal-end region 24 is more flexible and has lower torque transfer strength than the proximal region 26. To further increase flexibility, the distal-end region 24 of the sheath 22 may have a lower durometer material or a thinner wall.

Referring again to FIG. 2, a proximal portion of the distal-end region 24 of the sheath 22 overlaps the exposed portion of the middle layer 82 of the proximal region 26 and butts against the distal end of the outer layer 84 of the proximal region. The proximal portion of the distal-end region 24 is then bonded to the distal portion of the proximal region 26 to form one continuous sheath 22 through techniques that are well known to those skilled in the art, such as with epoxy. The proximal end 76 of the sheath 22 is bonded to the handle 42 (FIG. 1), such as with cyanoacrylate adhesive, or attached by some equivalent mechanical means.

With further reference to FIG. 2, the tip electrode 34 includes a substantially dome-shaped distal portion 88 and a substantially cylindrical proximal portion 90. The two portions 88, 90 are contiguous and are preferably formed as a single unitary structure. As previously mentioned, the tip electrode 34 includes the bore 48 for receiving the thermocouple/drive wires 46 and first steering tendon 54. The bore 48 penetrates the proximal surface 92 of the proximal portion 90. The proximal portion 90 also includes raised ridges 94 to aid in anchoring the tip electrode 34 to the sheath 22. The tip electrode 34 is formed from a biocompatible material having high thermal conductivity properties. Possible materials include silver, gold, chromium, aluminum, molybdenum, tungsten, nickel, platinum, and platinum/10% iridium.

Figure 5:
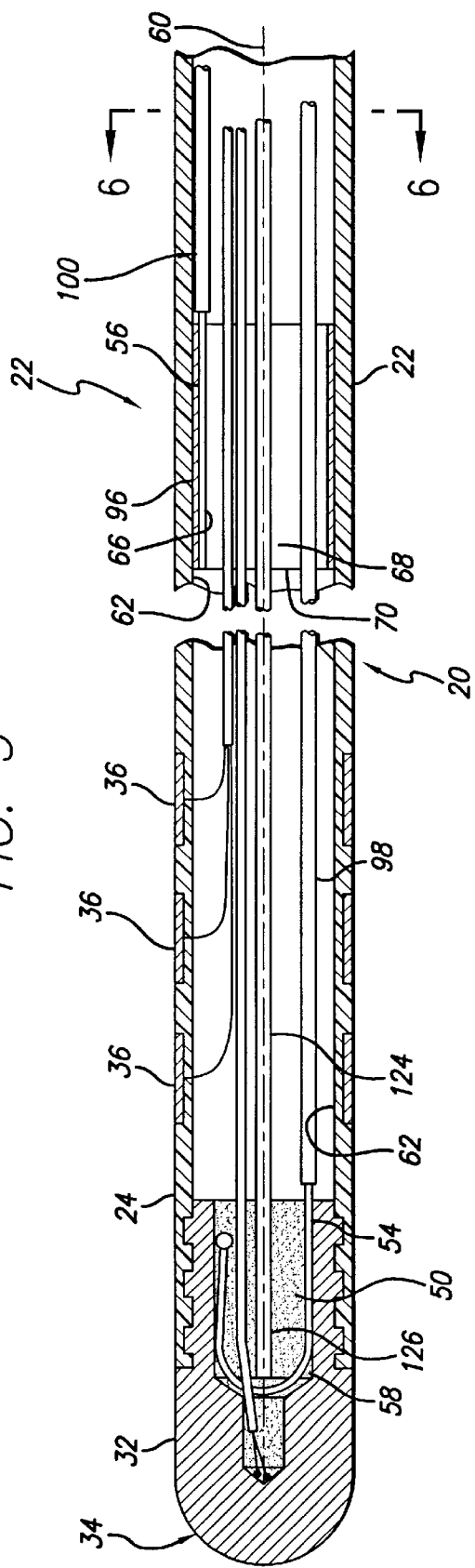
FIG. 5 is a cross-sectional plan view of the distal-end region of the catheter of FIG. 1 depicting the attachment points for the steering tendons, wherein the steering tendons are disposed approximately 180° apart and on opposite sides of the torque transfer system.

With reference to FIG. 5, the anchor band 70 has an inner surface 68 and an outer surface 96. The outer surface 96 of the anchor band 70 is roughened, for example, by machining or by a micro-blasting process, in order to improve adhesion properties. The anchor band 70 is preferably made from a metallic material, such as stainless steel.

In this embodiment, the anchor band 70 is located proximal to the most proximal band electrode 36. The distal end 66 of the second steering tendon 56 is welded, soldered, brazed, adhesively bonded, or otherwise attached to the inner surface 68 of the anchor band 70 and then the anchor band 70 is adhered to the inner surface 62 of the sheath 22 within the distal-end region 24, such as by melt-bonding, adhesives, or some equivalent mechanical means. Such placement puts the distal end 66 of the second steering tendon 56 at a location offset from the centerline 60 of the sheath 22 and proximate the inner surface 62 of the sheath 22. As will be discussed below in more detail, by placing the distal end 66 of the second steering tendon 56 at a location offset from the centerline 60 and proximate the inner surface 62 of the sheath 22, a relatively low amount of force applied to the second steering tendon 56 will generate a bending moment sufficient to deflect the distal-end region 24.

Figure 7:
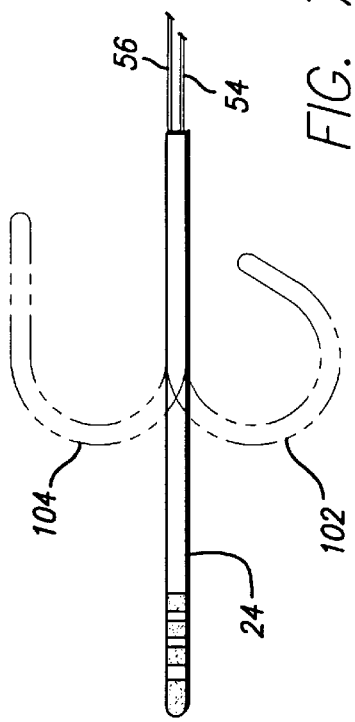
FIG. 7 is a schematic depicting the profiles that may be created within the distal-end region of the catheter of FIG. 5 when the first steering tendon and the second steering tendon are axially displaced in a proximal direction.

With continued reference to FIG. 5, the first steering tendon 54 and the second steering tendon 56 are both housed within the sheath 22, are offset from the centerline 60, and are located proximate the inner surface 62 of the sheath. The first steering tendon 54 is attached at a location distal to the second steering tendon 56. The general orientation of the steering tendons in the present embodiment is shown in the cross-sectional view of FIG. 6 where the first steering tendon 54 is located approximately 180° apart from the second steering tendon 56, on opposite sides of the flat ribbon 124. As shown in FIG. 7, having the steering tendons 54, 56 attached approximately 180° apart produces deflection profiles of the distal-end region 24 in opposite directions on opposite sides of the catheter 20. In this configuration, the catheter 20 steers in different directions when the steering tendons 54, 56 are axially displaced, thus the catheter is bidirectional.

With further reference to FIG. 5, the steering tendons 54, 56 may be formed from stainless steel wire having a diameter of approximately 0.2 mm. To reduce friction and thereby minimize the force required to steer the catheter 20, the two steering tendons 54, 56 are each enclosed within a respective sheath 98, 100. The sheaths 98, 100 cover substantially the entire length of the steering tendons 54, 56 and provide a relatively small clearance to permit the steering tendons to readily slide within the sheaths 98, 100. The sheaths include a tubular, polymeric material and are either coated or are formed of a low friction material, such as polytetrafluoroethylene (PTFE), known commercially as Teflon™.

For clarification purposes, in following discussions, the term "attachment point" in relation to the distal ends 58, 66 of the steering tendons 54, 56 refers to the distal end of the first steering tendon being secured within the distal tip 32 and the distal end of the second steering tendon being attached to the anchor band 70. The bending moments of the steering tendons increase as the distance between the centerline 60 of the catheter sheath 22 and the attachment points of the steering tendons increase. Therefore, in steerable catheters where the steering tendons are attached close to the centerline of the sheath, a relatively greater amount of force may be required to displace the steering tendons in order to deflect or change the profile of the distal-end region. In comparison, by having the distal ends 58, 66 of the steering tendons 54, 56 located at positions offset from the centerline 60 and proximate the inner surface 62 of the sheath 22, the bending moments of the steering tendons are increased. Thus, a relatively low amount of force is required to displace the steering tendons in order to deflect the distal-end region 24.

Referring again to FIG. 5, the distal end 58 of the first steering tendon 54 is secured to the inner wall 48 of the tip electrode 34 at a point away from the catheter centerline 60 and the distal end 66 of the second steering tendon 56 is secured to the inside surface 68 of an anchor band 70 also at a point away from the catheter centerline 60 and near or proximate the catheter wall 62. Both of the tendons 54, 56 run the length of the catheter 20 substantially parallel to the inner surface 62 of the catheter, away from the catheter centerline 60. Applying tension to the proximal end 72, 74 (FIG. 1) of either tendon 54, 56 results in the application of force along the length of the tendon to its distal end 58, 66 attachment point at the tip electrode 34 (first steering tendon) or anchor band 70 (second steering tendon). A tensile force applied to the tip electrode 88 by the first steering tendon 54 is reacted by compressive forces within the flat ribbon 124 and sheath 22. Because the first steering tendon's 54 attachment point within the tip electrode 88 is substantially offset from the centerline 60 of both the flat ribbon 124 and sheath 22, these opposing tensile and compressive forces create a bending moment that acts upon the tip electrode 88. This bending moment deflects the tip electrode 88 and is reacted by the combined bending stiffness of the sheath 22, flat ribbon 124, and other components inside the sheath. Increasing the tensile force on the first steering tendon 54 increases the deflection of the tip electrode 88, thereby decreasing the radius of curvature throughout the length of the sheath 22. The resulting steered profile 102 (FIG. 7) is essentially a circular arc. Similarly, a tensile force applied to the anchor band 70 by the second steering tendon 56 is reacted by forces within the sheath 22. Because the second steering tendon's 56 attachment point within the anchor band 70 is substantially offset from the centerline 60 of the sheath 22, a bending moment acts upon the anchor band. Because the anchor band 70 is affixed to the sheath 22, this bending moment deflects the sheath and is reacted by the combined bending stiffness of the sheath, flat ribbon 124, and other components within the sheath proximal the anchor band 70. Increasing the tensile force on the second steering tendon 56 increases the deflection of the sheath 22, thereby decreasing the radius of curvature over the section of sheath that is proximal to the anchor band 70. The resulting steered profile 104 (FIG. 7) is essentially a circular arc with a straight section beyond the anchor band 70.

Figure 8:
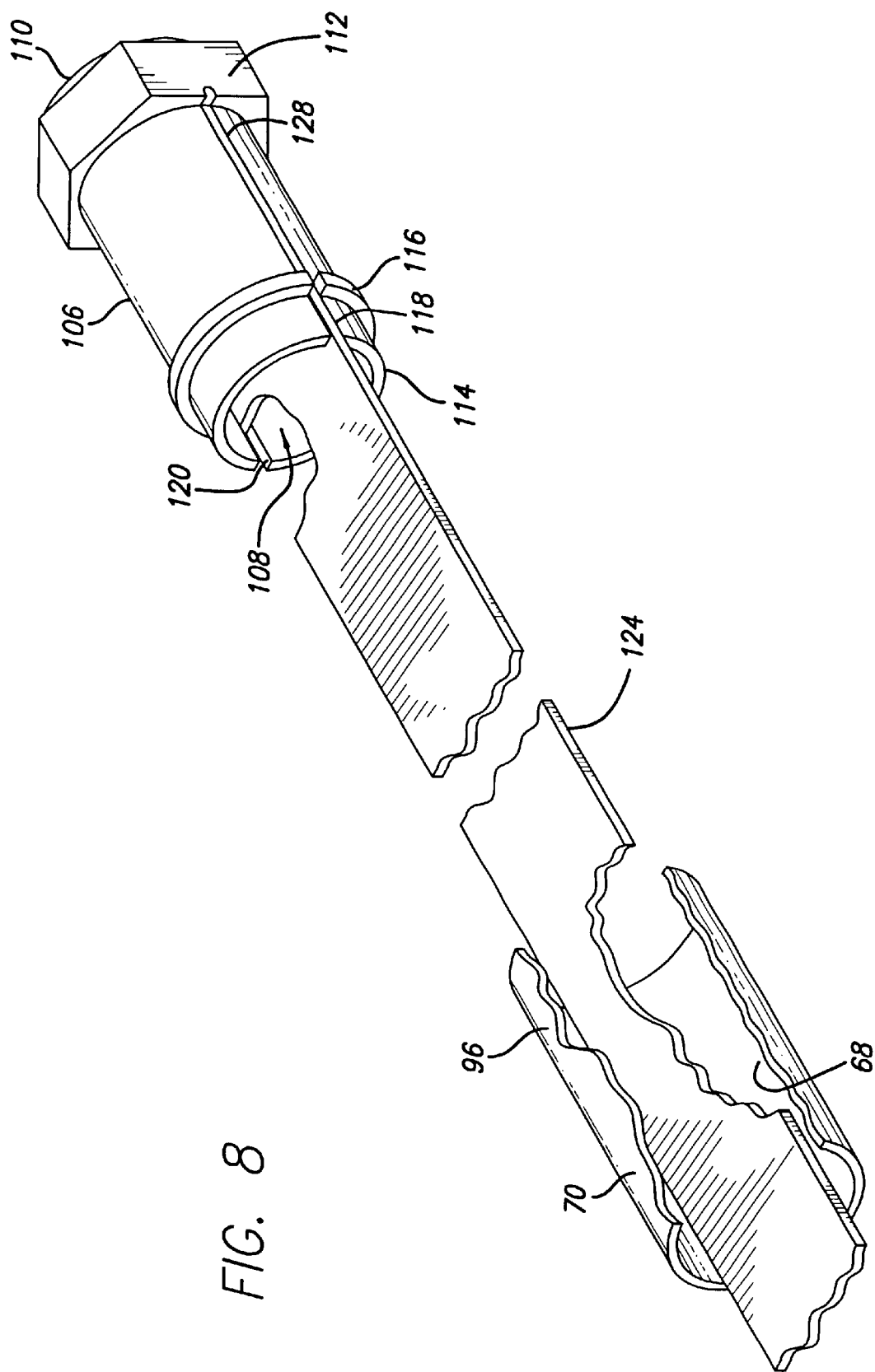
FIG. 8 is a tri-metric view with a broken-out section of the catheter of FIG. 1 depicting the detailed components of the torque transfer system including an eyelet, a ribbon and an anchor band with other items removed for clarity.

Referring to FIGS. 2 and 8, as previously mentioned, the torque transfer system includes the eyelet 106 and the flat ribbon 124. The torque transfer system is adapted to increase the torque transfer strength of the distal-end region 24 and to facilitate the transfer of torsional forces from the proximal region 26 of the sheath 22 to the distal-end region 24 of the sheath. The eyelet 106 is tubular in shape and includes a central lumen 108. A proximal end 110 of the eyelet 106 includes an enlarged, non-circular flange 112 with a substantially angular shape, such as a hexagon. The non-circular flange 112 has a cross-sectional diameter that is greater than the inner diameter of the sheath 22. Near the distal end 114 of the eyelet 106 is a circular flange 116 that protrudes outwardly. Extending through the distal end 114 of the eyelet 106 is a pair of longitudinal, diametrically opposed slots 118, 120. The eyelet 106 is preferably made from a metallic material, such as stainless steel. The eyelet 106 is installed into the central lumen 28 of the sheath 22, prior to the joining of the distal-end region 24 and the proximal region 26, by inserting the proximal-end 110 of the eyelet into the distal end 122 of the proximal region of the sheath until the circular flange 116 butts against the distal end of the proximal region. Such installation secures the non-circular flange 112 of the eyelet 106 within the sheath 22 by embedding itself into the inner surface 62 of the proximal region 26 of the sheath.

With continued reference to FIGS. 2 and 8, the flat ribbon 124 includes a distal end 126 and a proximal-end 128, and is preferably made from a resiliently deformable, shape-memory material, such as Nitinol. Such material permits the flat ribbon 124 to deflect with the distal-end region 24 of the sheath 22, yet the shape-memory aspect of the flat ribbon tends to return the flat ribbon, and also the catheter distal end, to the straight, or non-deflected, shape as shown in FIGS. 2 and 8. In one embodiment, the flat ribbon 124 includes a flattened Nitinol wire and has a substantially rectangular cross section. The distal end 126 of the flat ribbon 124 is attached to the distal-end region 24 of the sheath 22 and the proximal end 128 of the flat ribbon is attached to the proximal region 26 of the sheath. More specifically, the proximal-end 128 of the flat ribbon 124 is installed through the distal end 30 of the distal-end region 24, inserted into the slots 118, 120 within the eyelet 106, and bonded into place, such as with epoxy, or attached by an equivalent mechanical means. Further, lateral movement of the proximal-end 128 of the flat ribbon 124 is restricted by the inner surface 62 of the sheath 22. The distal end 126 of the flat ribbon 124 is installed into the bore 48 of the distal tip 32 and is bonded into place with the resin 50. In this fashion, the flat ribbon 124 bridges the entire distal-end region 24 between the proximal region 26 and the distal tip 32. Such installation positions the flat ribbon 124 along the centerline 60 of the distal-end region 24 of the sheath 22.

The torsional rigidity of the distal-end region 24 is significantly enhanced by the installation of the flat ribbon 124. As a result, rotations of the handle 42 (FIG. 1) by the operator are accurately transferred to the distal tip 32. More specifically, as the handle 42 is rotated, the torsional forces that are exerted transfer to the proximal region 26 of the sheath 22 because of the attachment means between the handle and the sheath. The braided stainless steel ribbons of the middle layer 82 (FIGS. 2 and 3) within the proximal region 26 transfers the torsional forces to the distal end 122 of the proximal region of the sheath 22. The torsional forces are then transferred to the eyelet 106 (FIGS. 2 and 8) by means of the non-circular flange 112 that is embedded within the distal end 122 of the proximal region 26. Since the embedded portion of the eyelet 106 is non-circular, the eyelet will not rotate freely within the proximal region 26 of the sheath 22. Therefore, the torsional forces are transferred from the eyelet 106 to the flat ribbon 124 (FIGS. 2 and 8) whose proximal end 128 is interrelated with the slots 118, 120 in the eyelet. Since the distal end 126 of the flat ribbon 124 is bonded into the bore 48 of the distal tip 32 (FIG. 2), the torsional forces are transferred to the distal tip. With the enhanced distal torque transfer provided by the flat ribbon 124, the torque imparted by the proximal region 26 is effectively transferred to the distal tip 32 without the meed for a middle layer of braided material within the distal-end region 24, such as the middle layer 82 of the proximal region. As is well known, additional layers increase stiffness, size, and cost. A significant advantage of the torque transfer system using the flat ribbon 124 is that rotational handle 42 movements will be accurately transferred to the distal tip 32. Thus, the operator can place the distal tip 32 of the catheter 20 at a desired location within a patient with greater precision and the possibility of harm to the patient due to an uncontrolled "whipping" type movement of the distal region is sharply reduced. Another advantage of having the flat ribbon 124 within the distal-end region 24 is that by rotating the handle 42 with the distal-end region in the deflected condition, the distal tip 32 can exert a relatively great amount of force against the desired location.

The profile of the distal-end region 24 can be adjusted by manipulating the steering controller 78 (FIG. 1), which axially displaces either the first steering tendon 54 or the second steering tendon 56 in the proximal direction. Axially displacing a steering tendon in the proximal direction causes that steering tendon to experience greater tension. The tensile load is transferred to the steering tendon's 54, 56 distal attachment point, where other components of the catheter 20 structure react with a compressive load essentially equal in magnitude to the tensile load applied by the steering tendon. The tensile and compressive loads exist within the steering tendon 54, 56 and certain other components of the catheter structure, respectively, at all locations that are proximal to the tendon's distal attachment point. In addition, a bending moment is also present because the steering tendon's 54, 56 distal attachment point, by design, does not coincide with the longitudinal axis or centerline 60 of the catheter shaft 22.

More specifically, if tension is applied to the first steering tendon 54, it carries a tensile load to its distal attachment point, the tip electrode 34. At the attachment point, that tensile load is reacted to by an equivalent compressive load that is carried by several components within the catheter 20 structure, notably the flat ribbon 124, eyelet 106, and proximal region 26 of the sheath 22. One effect of the essentially equal but opposite axial forces is that the overall length of the catheter 20 structure somewhat shortens while the overall length of the first steering tendon 54 slightly lengthens. A substantial bending moment is also present at the attachment point because the two forces are deliberately offset from one another by the distance between the flat ribbon 124 and first steering tendon 54. The bending moment increases as the distance between the flat ribbon 124 and the first steering tendon 54 increases. The effect of the bending moment is to deflect the distal tip 32 toward the side to which the first steering tendon 54 is attached. Such deflection is balanced by the inherent bending stiffness of certain components of the catheter 20 structure, notably the flat ribbon 124, and the distal-end region 24 of the sheath 22. As more tension is applied to the first steering tendon 54, the bending moment increases and thereby causes further deflection of the resisting components. Ultimately, the deflected shape 102 of the catheter's distal end resembles a circle (FIG. 7).

If tension is applied to the second steering tendon 56, it carries a tensile load to its distal attachment point, the anchor band 70. The tensile load at the attachment point is reacted to by an equivalent compressive load that is carried primarily by the eyelet 124 and the proximal region 26 of the sheath 22. The overall length of the compressive load carrying elements somewhat shortens while the overall length of the second steering tendon 56 somewhat lengthens. A substantial bending moment is generated at the second steering tendon's 56 distal attachment point, and its effect is to deflect the anchor band 70 toward the side to which the second steering tendon is attached. The deflection is balanced by the inherent bending stiffness of certain components of the catheter 20 structure, notably the distal-end region 24 of the sheath 22 and a portion of the flat ribbon 124. The distal portion of the flat ribbon 124 remains straight because the bending moment arises at the anchor band 70, which is located proximal the distal tip 32. As more tension is applied to the second steering tendon 56, the resulting bending movement increases and thereby causes further deflection of the resisting components. Ultimately, the deflected shape 104 of the catheter's distal end resembles a letter "U" (FIG. 7).

The bending or deflection profiles 102, 104 (FIG. 7) of the catheter are somewhat asymmetric, a result of the axial displacement between the distal end mounting locations of the steering tendons 54, 56. The degree of difference in the deflection profiles 102, 104 depends upon the location of the attachment point of the distal end 66 of the second steering tendon 56 in comparison to the first steering tendon 54. Thus, the steering profiles can be altered by changing the location of the attachment point of the distal end 66 of the second steering tendon 56.

The components within the catheter that experience steering deflection are designed accordingly. For example, the flat ribbon 124 is relatively wide and thin and made of a highly resilient material so it will easily bend in one plane and will recover elastically after extreme deflection. Similarly, the steering tendons 54, 56 possess a small diameter and are made of spring temper stainless steel.

Figure 6:
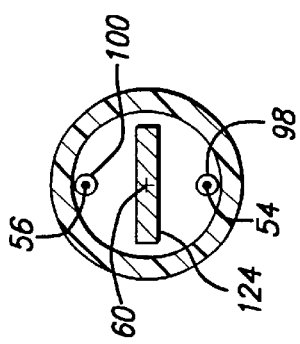
FIG. 6 is a cross-section view of the distal-end region depicting the steering tendons disposed approximately 180° apart and on opposite sides of the torque transfer system, taken along the line 6—6 from FIG. 5 with other items removed for clarity.

Alternatively, although not shown, the distal ends 58, 66 of the steering tendons 54, 56 may both be attached to the distal tip 32 or to the proximal anchor band 70 such that the points of attachment are 1) axially identical along the length of the sheath and 2) angularly displaced from each other along the circumference of the inner surface of the sheath. Such placement of the steering tendons 54, 56 causes the deflection profiles of the catheter 20 to be identical although they will be angularly displaced from each other. For example, when the distal ends 58, 66 of the steering tendons 54, 56 are attached approximately 180° apart along the inner surface of the sheath as shown in FIG. 6, but are attached such that the distal ends are located at the same axial distance from the steering controller 78, the deflections will be symmetric and occur in opposite directions.

Figure 9:
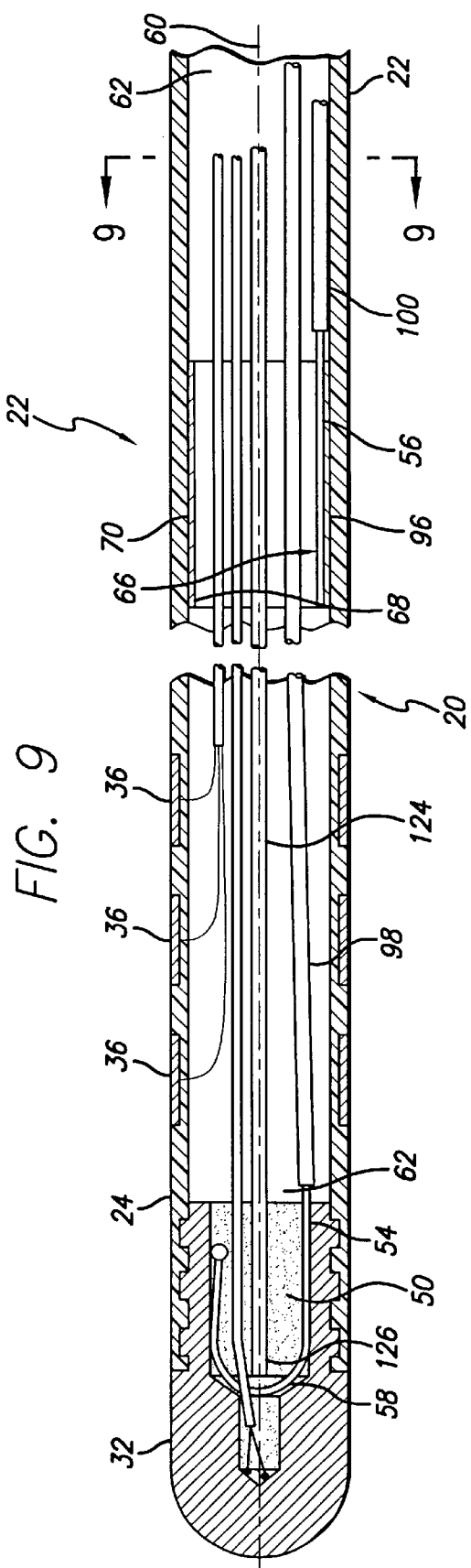
FIG. 9 is a cross-sectional plan view of the distal-end region of another configuration of the catheter of FIG. 1 depicting the attachment points for the steering tendons, wherein the steering tendons are disposed approximately angularly aligned.
Figure 11:
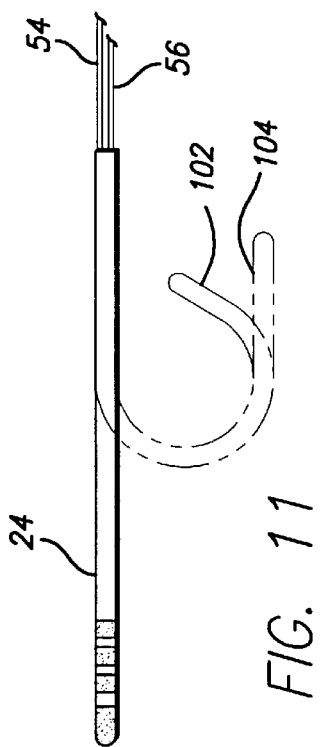
FIG. 11 is a schematic depicting the profiles that may be created within the distal-end region of the catheter of FIG. 9 when the first steering tendon and the second steering tendon are axially displaced in a proximal direction.
Figure 10:
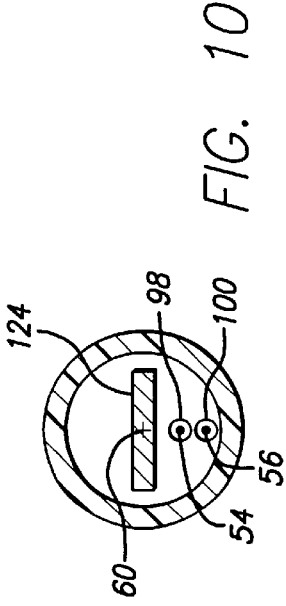
FIG. 10 is a cross-section view of the distal-end region depicting the steering tendons disposed approximately angularly aligned on the same side of the torque transfer system, taken along the line 10—10 from FIG. 9 with other items removed for clarity.

With reference to FIG. 9, an alternative embodiment of the catheter of FIG. 1 is depicted wherein both steering tendons 54, 56 are approximately angularly aligned on the same side of the flat ribbon 124. The first steering tendon 54 is attached at a location distal to that of the second steering tendon 56. The general orientation of the tendons 54, 56 is shown in the cross-sectional view of FIG. 10 where the first steering tendon 54 is located closer to the longitudinal centerline 60 of the catheter sheath 22 than the second steering tendon 56. As shown in FIG. 11, having the steering tendons 54, 56 approximately angularly aligned produces different deflection profiles on the same side of the catheter. In this configuration, the catheter 20 steers in the same direction when either steering tendon 54, 56 is axially displaced, thus the catheter deflection is unidirectional and asymmetric. However, the attachment of the first steering tendon 54 to the catheter sheath 22 at a position distal to the second steering tendon 56 permits a greater curl to the deflected distal end, as shown in FIG. 11. The first dashed profile 102 is achieved through axial movement of the first steering tendon 54 alone while the second dashed profile 104 is achieved through axial movement of the second steering tendon 56 alone.

Figure 12:
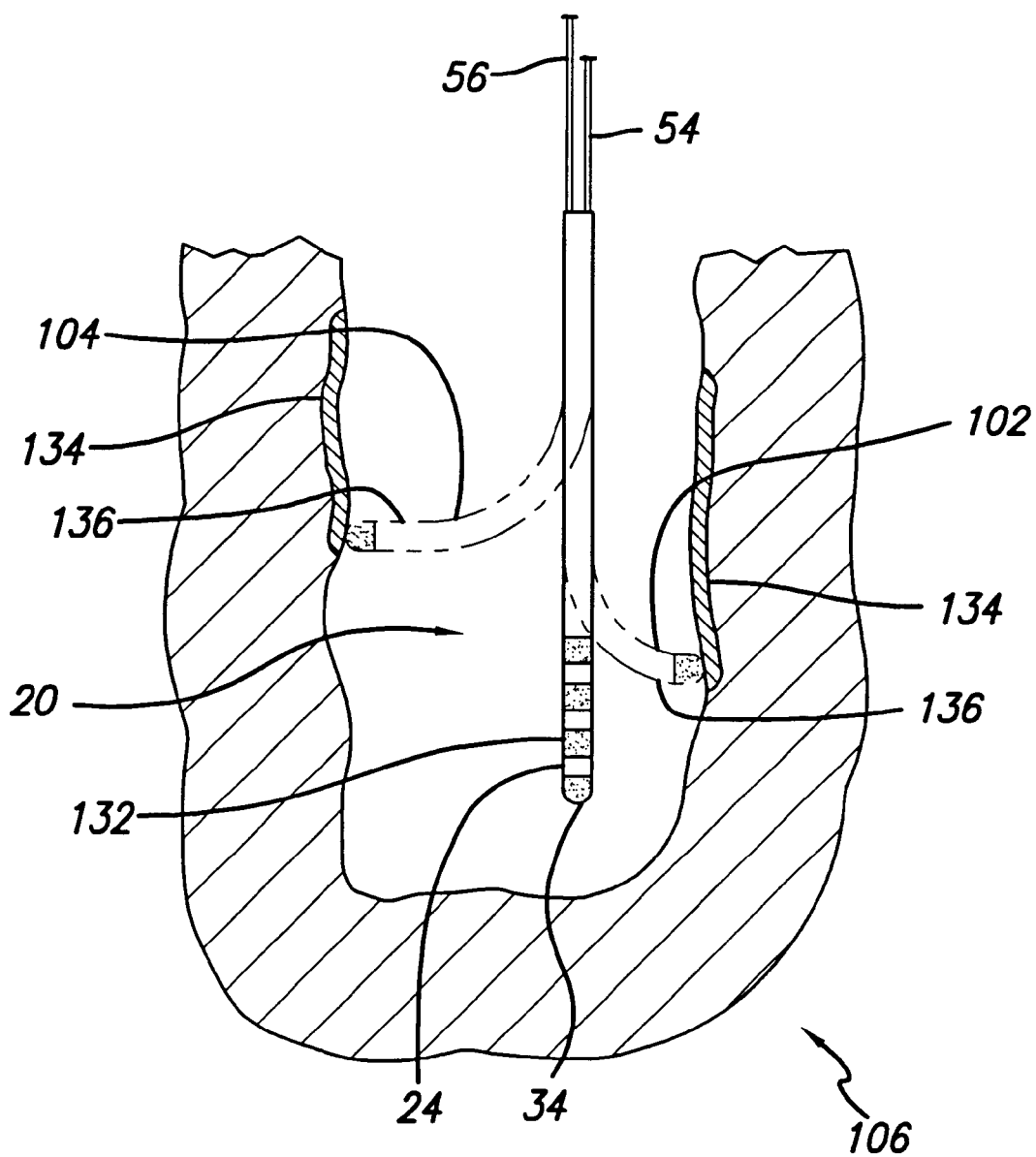
FIG. 12 is a schematic depicting the catheter of FIG. 1 in use in a biological cavity within a patient.

With reference to FIG. 12, in operation, a catheter 20 having bidirectional deflection configured in accordance with the invention is introduced into a biological site 130, such as the right atrium of the heart. During introduction, the catheter 20 is maintained in a substantially linear arrangement 132. While the distal end region 24 of the catheter 20 is being positioned near the area of target tissue 134 to be ablated, the distal-end region is deflected by pulling on the appropriate one of the steering tendons 54, 56, as previously described. Once the distal-end region 24 is adequately deflected 136 to establish contact between the tip electrode 34 and the area of target tissue 134, ablation energy is applied through the tip electrode. If the target tissue 134 comprises a linear segment, the catheter 20 is pulled in the proximal direction during the application of ablation energy to produce a lesion having length, as opposed to only a spot lesion.

Because the location of the attachment point of the first steering tendon 54 to the catheter sheath 22 is more distal than that of the second steering tendon 56 (see FIGS. 5 and 9), for an equal distance of axial translation of the steering tendons the first deflection profile 102 (see FIGS. 7 and 11) does not move the tip electrode 34 as far from the centerline 60 of a non-deflected catheter as does the second deflection profile 104. Also, the first deflection profile 102 may permit more force to be applied to the target site. Therefore, referring to FIG. 12, in instances where the target tissue 134 is located within a compact cavity within the patient, or a relatively higher amount of force is to be applied to the target tissue, it may be desirable to utilize the first deflection profile 102 of the catheter 20. Conversely, where the target tissue 134 is located within a more open cavity within the patient, or a relatively lower amount of force is to be applied to the target tissue, it may be desirable to utilize the second deflection profile 104 of the catheter 20. Hence, because of its ability to be configured with different distal-end deflection profiles 102, 104, the catheter 20 of the present invention may be used to form multiple lesions in different environments within a patient without the need of multiple catheters.

It will be apparent from the foregoing that, while particular forms of the invention have been illustrated and described, various modifications can be made without departing from the spirit and scope of the invention.

What is claimed is:

1. A catheter comprising:
    a sheath including a proximal region, a distal-end region having a distal tip, and a longitudinal centerline;
    a first steering tendon housed within the sheath, the first steering tendon having a first end attached to the distal-end region at a location offset from the centerline of the sheath, and a second end located at the proximal region of the sheath, wherein movement of the first steering tendon in the proximal direction causes the sheath distal-end region to deflect;
    a second steering tendon housed within the sheath, the second steering tendon having a first end attached to the distal-end region at a location offset from the centerline of the sheath, and a second end located at the proximal region of the sheath, wherein movement of the second steering tendon in the proximal direction causes the sheath distal-end region to deflect; and
    a torque transfer system adapted to transfer torsional forces from the proximal region of the sheath to the distal-end region of the sheath, the torque transfer system including a ribbon having a length which is less than the length of the sheath, the ribbon being housed within the distal-end region of the sheath and configured to deflect therewith, the ribbon having a first end attached to the distal tip of the sheath and a second end attached to a distal portion of the proximal region of the sheath.

2. The catheter of claim 1 wherein the ribbon is positioned along the centerline of the distal-end region of the sheath.

3. The catheter of claim 1 wherein the ribbon is formed of a resiliently deformable, shape-memory material.

4. The catheter of claim 1 wherein the ribbon has a substantially rectangular cross-section and the firs: steering tendon and the second steering tendon are attached proximate the inner surface of the sheath on opposite sides of the ribbon.

5. The catheter of claim 4 wherein the attachment point of the first steering tendon is distal the attachment point of the second steering tendon.

6. The catheter of claim 4 wherein the attachment point of the first steering tendon and the attachment point of the second steering tendon are axially aligned.

7. The catheter of claim 1 wherein the ribbon has a substantially rectangular cross-section and the first steering tendon and the second steering tendon are attached proximate the inner surface of the sheath on the same side of the ribbon.

8. The catheter of claim 7 wherein the attachment point of the first steering tendon is distal the attachment point of the second steering tendon.

9. The catheter of claim 1 wherein the torque transfer system further comprises an eyelet secured within the proximal region of the sheath and the second end of the ribbon is secured within the eyelet.

10. The catheter of claim 9 wherein the eyelet comprises a non-circular shape proximal end having a maximum cross-sectional diameter greater than the inner diameter of the sheath.

11. The catheter of claim 10 wherein the non-circular shape comprises a substantially angular shape.

12. The catheter of claim 11 wherein the angular shape comprises a substantially hexagonal shape.

13. A catheter comprising:
    a sheath including a proximal region and a distal-end region having a distal tip;
    a first steering tendon housed within the sheath, the first steering tendon having a first end attached to the distal-end region at a point proximate the inner surface of the sheath, and a second end exiting the proximal end of the sheath, wherein movement of the first steering tendon in a proximal direction causes die sheath distal-end region to deflect;
    a second steering tendon housed within the sheath, the second steering tendon having a first end attached to the distal-end region at a point proximate the inner surface of the sheath and proximal the attachment point of the first steering tendon, and a second end exiting the proximal end of the sheath, wherein movement of the second steering tendon in the proximal direction causes the sheath distal-end region to deflect; and
    a ribbon having a length which is less than the length of the sheath, the ribbon being housed within the distal-end region of the sheath and configured to deflect therewith, the ribbon having a first end attached to the distal tip of the sheath and a second end attached to a distal portion of the proximal region of the sheath.

14. The catheter of claim 13 wherein the distal-end region of sheath comprises a longitudinal centerline and the ribbon is positioned along the centerline.

15. The catheter of claim 13 wherein the ribbon is formed of a resiliently deformable, shape-memory material.

16. The catheter of claim 13 wherein the ribbon has a substantially rectangular cross-section and the first and second steering tendons are attached on opposite sides of the ribbon.

17. The catheter of claim 13 wherein the ribbon has a substantially rectangular cross-section and the first steering tendon and the second steering tendon are attached on the same side of the ribbon.

18. The catheter of claim 13 further comprising an eyelet housed within the proximal region of the sheath at the distal end of the proximal region wherein the second end of the ribbon is secured within the eyelet.

19. The catheter of claim 18 wherein the eyelet comprises a non-circular shape proximal end having a maximum cross-sectional diameter greater than the inner diameter of the sheath.

20. The catheter of claim 13 wherein the first steering tendon is secured within the distal tip of the distal-end region.

21. The catheter of claim 13 further comprising:
an anchor band positioned within the distal-end region, proximal the distal tip;
wherein the first end of the second steering tendon is attached to the anchor band.

22. A catheter for use with biological tissue, the catheter comprising:
a sheath including a proximal region having a first torque transfer strength and a distal-end region having a distal tip and a second torque transfer strength less than the first torque transfer strength;
at least one electrode located in the distal-end region for transferring energy to the biological tissue;
a first steering tendon housed within the sheath, the first steering tendon having a first end attached to the distal-end region at a point proximate the inner surface of the sheath, and a second end exiting the proximal end of the sheath, wherein movement of the first steering tendon in a proximal direction causes the sheath distal-end region to deflect;
a second steering tendon housed within the sheath, the second steering tendon having a first end attached to the distal-end region at a point proximate the inner surface of the sheath and proximal the attachment point of the first steering tendon, and a second end exiting the proximal end of the sheath, wherein movement of the second steering tendon in the proximal direction causes the sheath distal-end region to deflect; and
a torque transfer system adapted to increase the torque transfer strength of the distal-end region to facilitate the transfer of torsional forces from the proximal region to the distal-end region, the torque transfer system including a ribbon having a length which is less than the length of the sheath, the ribbon being housed within the distal-end region of the sheath and configured to deflect therewith, the ribbon having a first end attached to the distal tip of the sheath and a second end attached to a distal portion of the proximal region of the sheath.

23. The catheter of claim 22 wherein the sheath comprises a centerline and the ribbon is positioned along the centerline.

24. The catheter of claim 22 wherein the ribbon is formed of a resiliently deformable, shape-memory material.

25. The catheter of claim 22 wherein the ribbon has a substantially rectangular cross-section and the first steering tendon and the second steering tendon are attached proximate the inner surface of the sheath on opposite sides of the ribbon.

26. The catheter of claim 22 wherein the ribbon has a substantially rectangular cross-section and the first steering tendon and the second steering tendon are attached proximate the inner surface of the sheath on the sane side of the ribbon.

27. The catheter of claim 22 wherein the torque transfer system further comprises an eyelet secured within the proximal region of the sheath and the second end of the ribbon is secured within the eyelet.

28. The catheter of claim 27 wherein the eyelet comprises a non-circular shape proximal end having a cross-sectional diameter greater than the inner diameter of the sheath.

29. A catheter for use with biological tissue, the catheter comprising:
a sheath including a proximal region having a first torque transfer strength and a distal-end region having a second torque transfer strength less than the first torque transfer strength, and a centerline throughout the length of the sheath;
at least one electrode located in the distal-end region for transferring energy to the biological tissue;
a first steering tendon housed within the sheath, the first steering tendon having a first end attached to the distal-end region at a point proximate the inner surface of the sheath, and a second end exiting the proximal end of the sheath, wherein movement of the first steering tendon in a proximal direction causes the sheath distal-end region to deflect;
a second steering tendon housed within the sheath, the second steering tendon having a first end attached to the distal-end region at a point proximate the inner surface of the sheath and proximal the attachment point of the first steering tendon, and a second end exiting the proximal end of the sheath, wherein movement of the second steering tendon in the proximal direction causes the sheath distal-end region to deflect;
an eyelet secured within the proximal region of the sheath having a non-circular shape proximal end having a cross-sectional diameter greater than the inner diameter of the sheath; and
a ribbon positioned along the centerline of the sheath and housed within the distal-end region of the sheath and configured to deflect therewith, the ribbon having a first end secured within the distal tip of the distal-end region and a second end secured within the eyelet.

30. The catheter of claim 29 wherein the ribbon is formed of a resiliently deformable, shape-memory material.

31. The catheter of claim 29 wherein the ribbon has a substantially rectangular cross-section and the first steering tendon and the second steering tendon are attached proximate the inner surface of the sheath on opposite sides of the ribbon.

32. The catheter of claim 29 wherein the ribbon has a substantially rectangular cross-section and the first steering tendon and the second steering tendon are attached proximate the inner surface of the sheath on the same side of the ribbon.

* * * * *

UNITED STATES PATENT AND TRADEMARK OFFICE
CERTIFICATE OF CORRECTION

PATENT NO.      : 6,605,086 B2
DATED           : August 12, 2003
INVENTOR(S)     : Robert C. Hayzelden et al.

It is certified that error appears in the above-identified patent and that said Letters Patent is hereby corrected as shown below:

Title page,
Item [56], References Cited, U.S. PATENT DOCUMENTS, add the following:
-- 5,385,148   1/1995   Lesh et al.
   5,397,304   3/1995   Truckai, Csaba
   5,715,817   2/1998   Stevens-Wright et al. --.

Signed and Sealed this

Twenty-eighth Day of October, 2003

JAMES E. ROGAN
*Director of the United States Patent and Trademark Office*